United States Patent
Khoobehi et al.

(10) Patent No.: US 7,949,387 B2
(45) Date of Patent: May 24, 2011

(54) METHOD FOR EVALUATING RELATIVE OXYGEN SATURATION IN BODY TISSUES

(75) Inventors: Bahram Khoobehi, Metairie, LA (US); James M. Beach, Slidell, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 1031 days.

(21) Appl. No.: 10/593,175

(22) PCT Filed: Mar. 18, 2005

(86) PCT No.: PCT/US2005/009185
§ 371 (c)(1),
(2), (4) Date: Feb. 28, 2007

(87) PCT Pub. No.: WO2005/092008
PCT Pub. Date: Oct. 6, 2005

(65) Prior Publication Data
US 2008/0255457 A1    Oct. 16, 2008

Related U.S. Application Data

(60) Provisional application No. 60/554,456, filed on Mar. 19, 2004.

(51) Int. Cl.
*A61B 6/00* (2006.01)
(52) U.S. Cl. ......... 600/476; 600/322; 600/323; 600/475
(58) Field of Classification Search .................. 600/322, 600/323, 475, 476
See application file for complete search history.

(56) References Cited

U.S. PATENT DOCUMENTS 5,353,790 A    10/1994    Jacques et al. ................ 600/315
(Continued)

FOREIGN PATENT DOCUMENTS

DE    4433827    3/1996

OTHER PUBLICATIONS

Blumenroder, S. et al., "The influence of intraocular pressure and systemic oxygen tension on the intravascular pO2 of the pig retina as measured with phosphorescence imaging," Surv. Ophthalmol., vol. 42, pp. S118-S126 (1997).

(Continued)

*Primary Examiner* — Tse Chen
*Assistant Examiner* — Baisakhi Roy
(74) *Attorney, Agent, or Firm* — Bonnie J. Davis; John H. Runnels

(57) ABSTRACT

A new method was discovered to analyze continuous spectral curves to determine relative hemoglobin oxygen saturation, using spectral curves collected from a continuous range of wavelengths from about 530 nm to about 584 nm, including spectra from transmitted or reflected light. Using isosbestic points and curve areas, a relative saturation index was calculated. With this method, noninvasive, in vivo measurement of relative oxygen saturation was made using light reflected from blood vessels in the eye and to map and measure relative changes in hemoglobin oxygen saturation in primate retinal vessels and optic nerve head in response to controlled changes in inspired oxygen and intraocular pressure (IOP). This method could also measure oxygen saturation from other blood vessels that reflect light sufficient to give a clear spectra from the blood hemoglobin. Changes in blood oxygen saturation can be monitored with this method for early detection of disease.

13 Claims, 11 Drawing Sheets

U.S. PATENT DOCUMENTS

| | | | | |
|---|---|---|---|---|
| 5,355,880 | A | 10/1994 | Thomas et al. | 600/326 |
| 5,553,615 | A | 9/1996 | Carim et al. | 600/324 |
| 5,919,132 | A | 7/1999 | Faubert et al. | 600/318 |
| 5,931,779 | A * | 8/1999 | Arakaki et al. | 600/310 |
| 5,983,120 | A | 11/1999 | Groner et al. | 600/310 |
| 6,198,532 | B1 | 3/2001 | Cabib et al. | 356/456 |
| 6,276,798 | B1 | 8/2001 | Gil et al. | 351/206 |
| 6,419,361 | B2 | 7/2002 | Cabib et al. | 351/221 |
| 6,556,853 | B1 | 4/2003 | Cabib et al. | 600/407 |
| 7,333,842 | B2 | 2/2008 | Schweitzer et al. | 600/336 |
| 7,400,918 | B2 * | 7/2008 | Parker et al. | 600/323 |
| 7,657,292 | B2 * | 2/2010 | Baker et al. | 600/310 |
| 7,751,039 | B2 * | 7/2010 | Ramanujam et al. | 356/244 |
| 2008/0132771 | A1 * | 6/2008 | Parker et al. | 600/323 |
| 2008/0255457 | A1 * | 10/2008 | Khoobehi et al. | 600/476 |

OTHER PUBLICATIONS

Crittin, M. et al., "Hemoglobin oxygen saturation (So2) in the human ocular fundus measured by reflectance oximetry: preliminary data in retinal veins," Klin. Monatsbl. Augenheilkd, vol. 291, pp. 289-291 (2002).

Khoobehi, B. et al., "Hyperspectral Imaging of oxygen saturation in the optic nerve head, retina, and choriod," Abstract presented May 7, 2003 at Association for Research in Vision and Ophthalmology.

Yoneya, A. et al., "Retinal oxygen saturation levels in patients with central retinal vein occlusion," Ophthalmology, vol. 109, pp. 1521-1526 (2002).

Beach, J.M. et al., "Oximetry of retinal vessels by dual-wavelength imaging: calibration and influence of pigmentation, " J. Appl. Physiol., vol. 86, pp. 748-758 (1999).

Cioffi, G. A. et al., "Optic nerve blood flow in glaucoma," Semin. Ophthalmol., vol. 14, No. 3, pp. 164-170 1999.

Delori, F.C., "Noninvasive technique for oximetry of blood in retinal vessels," Appl. Optics, vol. 27, pp. 1113-1125 (1998).

Delori, F.C., "Reflectometry measurements of the optic disc blood volume, " in Ocular Blood Flow in Glaucoma. Means, Methods and Measurements, G. N. Lambrou, E. L. Greve eds., Berkely, CA, Kugler and Ghedini, pp. 155-163 (1989).

Delori, F.C. et al., "Spectral reflectance of the human ocular fundus," Appl. Optics, vol. 28, pp. 1061-1077 (1989).

Denninghoff, K.R. et al., "Retinal imaging techniques in diabetes," Diabetes Technol. Ther., vol. 2, pp. 111-113 (2000).

Harris, A. et al., "Simultaneous management of blood flow and IOP in glaucoma," Acta Ophthalmol. Scand., vol. 79, pp. 336-341 (2001).

Hayreh, S.S., "Factors influencing blood flow in the optic nerve head," J. Glaucoma, vol. 6, pp. 412-425 (1997).

Hickam, J.B. et al., "A study of retinal venous blood oxygen saturation in human subjects by photographic means," Circulation, vol. 27, pp. 375-383 (1963).

Hickam, J. et al., "Studies of the retinal circulation in man: observations on vessel diameter, arteriovenous oxygen difference, and mean circulation time," Circulation, vol. 33, pp. 302-316 (1966).

Khoobehi, B. et al., "Hyperspectral imaging for measurement of oxygen saturation in the optic nerve head," Investigative Ophthalmology and Visual Science, vol. 45, pp. 1464-1472 (2004).

Khoobehi, B. et al., "Non-invasive measurement of oxygen saturation in optic nerve head tissue," Proc. SPIE, vol. 5325, pp. 104-110, Optical Diagnostics and Sensing IV; Jun. 2004.

Schweitzer, D. et al., "A new method for the measurement of oxygen saturation at the human ocular fundus," Int. Ophthalmol., vol. 23, pp. 347-353. (2001).

Schweitzer, D. et al., "In vivo measurement of the oxygen saturation of retinal vessels in healthy volunteers," IEEE Trans Biomed Eng., vol. 46, pp. 1454-1465 (1999) $30.

Stefansson, E. et al., "Optic nerve oxygen tension in pigs and the effect of carbonic anhydrase inhibitors," Invest Ophthalmol. Vis. Sci., vol. 40, pp. 2756-2762 (1999).

Stefansson, E. et al., "Oxygenation and vasodilation in relation to diabetic and other proliferative retinopathies," Ophthalmic Surg., vol. 14, pp. 209-226 (1983).

Tiedeman, J.S. et al., "Retinal oxygen consumption during hyperglycemia in patients with diabetes without retinopathy," Ophthalmology, vol. 105, pp. 31-36 (1998).

* cited by examiner

US 7,949,387 B2

METHOD FOR EVALUATING RELATIVE OXYGEN SATURATION IN BODY TISSUES

This is the United States national stage of international application PCT/US2005/009185, filed 18 Mar. 2005, which claims the benefit of the 19 Mar. 2004 filing date of U.S. provisional application Ser. No. 60/554,456, under 35 U.S.C. §119(e).

The development of this invention was partially funded by grants R03EY012887 and P30EY02377 from the National Eye Institute, National Institutes of Health, Bethesda, Md.; and from a Space Product Development grant from the National Aeronautics and Space Administration. The Government has certain rights in this invention.

TECHNICAL FIELD

This invention pertains to a method to measure relative changes in blood oxygen saturation using hemoglobin spectral curves generated from reflected light from in vivo blood vessels, e.g., retinal macro- and micro-circulation.

BACKGROUND ART

The oxygen supply of the retina is provided by both the choroidal and retinal circulation. Because of the high oxygen needs of the retina, any alteration in circulation such as seen in diabetic retinopathy, hypertension, sickle cell anemia, and vascular diseases can result in impairment. Pathological conditions in the retina and optic nerve head (ONH) can cause vision loss and blindness. Both structures have a high demand for oxygen, and loss of the normal oxygen supply through vascular insufficiency is believed to play an important role in retinal and ONH pathology. See, G. A. Cioffi et al., "Optic nerve blood flow in glaucoma," *Semin. Ophthalmol.*, Vol. 14, no. 3, pp. 164-170 (1999); A. Harris et al., "Simultaneous management of blood flow and IOP in glaucoma," *Acta Ophthalmol. Scand.*, Vol. 79, pp. 336-341 (2001); and S. S. Hayreh, "Factors influencing blood flow in the optic nerve head," *J. Glaucoma*, Vol. 6, pp. 412-425 (1997). Hypoxia of the retina and ONH is believed to be a factor in the development of ocular vascular disorders such as diabetic retinopathy, arterial venous occlusion disease, and glaucoma. See, K. R. Denninghoff et al., "Retinal imaging techniques in diabetes," *Diabetes Technol. Ther.*, Vol. 2, pp. 111-113 (2000); E. Stefansson et al., "Oxygenation and vasodilation in relation to diabetic and other proliferative retinopathies," *Ophthalmic Surg.*, Vol. 14, pp. 209-226 (1983); A. Yoneya et al., "Retinal oxygen saturation levels in patients with central retinal vein occlusion," *Ophthalmology*, Vol. 109, pp. 1521-1526 (2002); and E. Stefansson et al., "Optic nerve oxygen tension in pigs and the effect of carbonic anhydrase inhibitors," *Invest Opthalmol. Vis. Sci.*, Vol. 40, pp. 2756-2762 (1999). The ability to obtain relative measurements of oxygen saturation in the human ocular fundus could aid diagnosis and monitoring of these and other disorders. For example, measurement of changes in retinal and ONH oxygen saturation under controlled conditions could establish relationships between oxygen consumption, blood sugar levels, and vascular autoregulatory function in diabetic retinopathy. Assessment of oxygenation in the ONH may facilitate early detection of the onset of glaucoma, a disease in which timely diagnosis is crucial for effective treatment.

Measurements of oxygen tension ($pO_2$) in the ONH have been performed using $O_2$-sensitive microelectrodes inserted into the eye. See, e.g., E. Stefansson et al., "Optic nerve oxygen tension in pigs and the effect of carbonic anhydrase inhibitors," *Invest. Ophthalmol. Vis. Sci.*, Vol. 40, pp. 2756-2762 (1999). Although this technique is accurate and can determine $pO_2$ distribution in three dimensions, its invasive nature limits its use to animal models and precludes clinical applications. Another technique involving injection of a phosphorescent dye has been used to study $pO_2$ in the retinal and choroidal vessels, as well as the microvasculature of the ONH rim. See, e.g., S. Blumenroder et al., "The influence of intraocular pressure and systemic oxygen tension on the intravascular pO2 of the pig retina as measured with phosphorescence imaging," *Surv. Opthalmol.*, Vol. 42, pp. S118-S126 (1997). However, use of the dye in humans has yet to be approved.

Imaging techniques based on spectral changes of oxygenated hemoglobin ($HbO_2$) and reduced hemoglobin (Hb) have been employed in humans to assess oxygen saturation in the ocular fundus, and in retinal artery/vein pairs. See Yoneya et al., (2002); and J. M. Beach et al., "Oximetry of retinal vessels by dual-wavelength imaging: calibration and influence of pigmentation," *J. Appl. Physiol.*, Vol. 86, pp. 748-758 (1999). These methods have been based most often on recordings at several discrete wavelengths chosen for their relative sensitivity to changes in oxygen saturation. See, M. Crittin et al., "Hemoglobin oxygen saturation (So2) in the human ocular fundus measured by reflectance oximetry: preliminary data in retinal veins," *Klin. Monatsbl. Augenheilkd*, Vol. 291, pp. 289-291 (2002); F. C. Delori, "Noninvasive technique for oximetry of blood in retinal vessels," *Appl. Optics*, Vol. 27, pp. 1113-1125 (1998); J. B. Hickam et al., "A study of retinal venous blood oxygen saturation in human subjects by photographic means," *Circulation*, Vol. 27, pp. 375-383 (1963); J. Hickam et al., "Studies of the retinal circulation in man: observations on vessel diameter, arteriovenous oxygen difference, and mean circulation time," *Circulation*, Vol. 33, pp. 302-316 (1966); and J. S. Tiedeman et al., "Retinal oxygen consumption during hyperglycemia in patients with diabetes without retinopathy," *Opthalmology*, Vol. 105, pp. 31-36 (1998).

Full spectral methods, employing a continuous range of wavelengths, have been used to record the reflectance profile versus wavelength from the ocular fundus. See, F. C. Delori, "Reflectometry measurements of the optic disc blood volume," in *Ocular Blood Flow in Glaucoma Means, Methods and Measurements*, G. N. Lambrou, E. L. Greve eds., Berkely, Calif., Kugler and Ghedini, pp. 155-163 (1989); and F. C. Delori et al., "Spectral reflectance of the human ocular fundus," *Appl. Optics*, Vol. 28, pp. 1061-1077 (1989). Full spectral imaging technique has also been employed to measure oxygen saturation in retinal arteries and veins under various conditions. See D. Schweitzer et al., "In vivo measurement of the oxygen saturation of retinal vessels in healthy volunteers," *IEEE Trans Biomed Eng.*, Vol. 46, pp. 1454-1465 (1999); and D. Schweitzer et al., "A new method for the measurement of oxygen saturation at the human ocular fundus," *Int. Ophthalmol.*, Vol. 23, pp. 347-353. (2001). Oxygen saturation in the ocular fundus has been mapped using Fourier transform spectral imaging. See, Yoneya et al., (2002). The full spectral technique employed most often uses a high resolution imaging spectrograph to collect the spectral information from a band of tissue in a single spatial dimension. The method acquires data rapidly and is applicable for use in human subjects. See Schweitzer et al., (1999); and Schweitzer et al., (2001).

DISCLOSURE OF INVENTION

We have discovered a new method to analyze continuous spectral curves to determine relative hemoglobin oxygen saturation. The method uses spectral curves collected from a continuos range of wavelengths from about 530 nm to about 584 nm, including spectra from transmitted or reflected light. Using isosbestic points and curve areas, a relative saturation index was calculated. With this method, noninvasive, in vivo measurement of relative oxygen saturation was using light reflected from blood vessels in the eye. This method could also measure oxygen saturation from other blood vessels that reflect light sufficient to give a clear spectra from the blood hemoglobin, e.g., skin, tongue, or intestine. This method was used in connection with hyperspectral imaging to generate two-dimensional maps of tissues indicating relative hemoglobin oxygen saturation. In particular, this method was used to map and measure relative changes in hemoglobin oxygen saturation in primate retinal vessels and optic nerve head in response to controlled changes in inspired oxygen and intraocular pressure (TOP). Changes in blood oxygen saturation can be monitored with this method for early detection of disease, e.g., diabetic retinopathy or glaucoma. This method could also be used to monitor oxygen treatments for wounds or burns.

MODES FOR CARRYING OUT THE INVENTION

Figure 1:
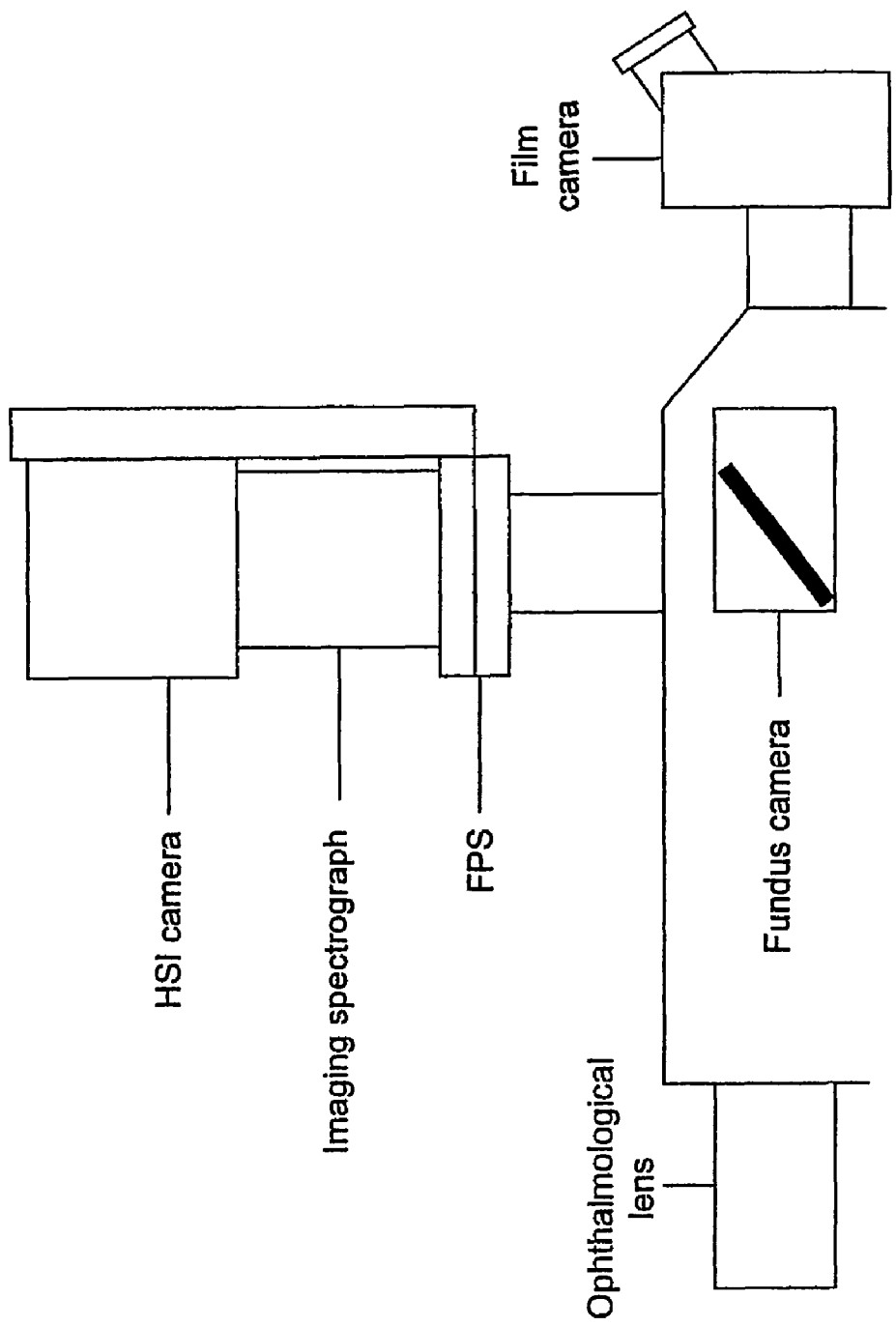
FIG. 1 illustrates the hyperspectral imaging system in relation to the fundus camera.

The optic nerve head (ONH) and overlying vessels in cynomolgus monkey eyes were imaged using a fundus camera attached to a hyperspectral imaging system. Images were acquired with inspiration of room air and pure oxygen, and at controlled intraocular pressures (IOP) of 15 mm Hg (normal) and 60 mm Hg (sustained for up to 5 minutes). Changes in relative blood oxygen saturation in the vessels and ONH were assessed from reflectance spectra. Saturation maps were derived from contributions of oxygenated and deoxygenated hemoglobin spectral signatures extracted from hyperspectral images. The results obtained with hyperspectral imaging were compared with known experimental outcomes.

Pure oxygen markedly increased oxygen saturation in veins; increases in arteries and the ONH were smaller. The results obtained with hyperspectral image analysis agreed with known changes in oxygen saturation from breathing experiments. Raising intraocular pressure (IOP) reduced saturation in all structures and resulted in profound desaturation of arteries. During sustained high IOP, a rebound in saturation was observed in the ONH. Spatial maps clearly showed the saturation changes in arteries, veins, and surrounding tissues.

Using this same method, relative oxygen saturation in blood vessels from other areas of the body could be measured both in one and two dimensions. If measured in two dimensions, as in hyperspectral imaging as discussed in U.S. Pat. No. 6,276,798, a two-dimensional map can indicate the relative oxygen saturation. Measurement of oxygen saturation can be used as an indication of disease or a predictor of disease, e.g., diabetic retinopathy, glaucoma, ulcer, etc. It can also be used to assess the effectiveness of hyperbaric oxygen treatment of flesh wounds or burns by monitoring the changes in blood oxygen in the blood vessels near the wound or burn. Since the hemoglobin under normal conditions occurs inside the blood vessels, this method can also be used to enhance the detail of the vasculature in a tissue when using hyperspectral imaging to produce spectral maps.

EXAMPLE 1

Materials and Methods

Animals. The use of animals in this study was approved by the Louisiana State University Health Sciences Center Institutional Animal Care and Use Committee and conformed to current standards in the use of animals in ophthalmic and vision research.

Two cynomolgus monkeys with normal eyes were used. The monkeys were anesthetized, and their eyes dilated. The initial opthalmologic examination included fluorescein angiography, color and red-free fundus photography, and slit-lamp examination of the fundus. To measure oxygen saturation of the optic nerve head (ONH) and paired retinal vessels, a contact lens was placed on the cornea to prevent drying, and reflectance hyperspectral imaging measurements as described below were obtained in one eye of each monkey. During imaging, pure oxygen was administered to one monkey to directly control blood oxygen saturation, and intraocular pressure (IOP) was controlled in the other monkey using methods described below.

Systemic Oxygen Saturation. An ear oximeter probe (Ohmeda 3700, Wallingford, Conn.) was placed on the monkey's earlobe to measure systemic oxygenation. A tracheal tube was positioned at the trachea and connected to a small-animal breathing chamber (Quantiflex; MDS Matrx Co., New York City, N.Y.). The oxygen chamber was supplied through a pressure regulator from an oxygen tank at a rate of 3 L/min at atmospheric pressure. This procedure brought the oximeter reading to 100% saturation. Hyperspectral images were obtained as described below while the monkey breathed room air and during inspiration of pure oxygen.

Intraocular pressure (IOP). To raise IOP, a 27-gauge needle was inserted into the anterior chamber of the eye under slit lamp examination. The needle was connected to a 500-ml reservoir containing saline solution with 0.1 ml gentamicin (40 mg/ml), 0.03 ml clindamycin (150 mg/ml), and 4 ml dexamethasone (4 mg/ml). IOP was raised by elevating the reservoir. IOP was monitored by means of a tonometer (Tonopen XL; Medtronic, Jacksonville, Fla.). Imaging was performed at normal IOP (15±2 mm Hg) and high IOP (60±2 mm Hg), close to the pressure needed to stop vessel perfusion. High pressure was maintained for no more than four minutes, while recordings were made at one minute intervals.

EXAMPLE 2

Hyperspectral Imaging System

Fundus Camera. The retina was illuminated with the internal tungsten aiming light of a fundus viewing camera (TRC-50vt, Topcon, Japan), similar to the procedure described in U.S. Pat. Nos. 5,919,132; and 6,276,798. Images were acquired using this camera with an opthalmologic lens and a c-mount through the vertical path of the camera. Hyperspectral images were obtained through the vertical viewing port using an imaging spectrograph and digital camera, as described below. FIG. 1 shows the components and position of the hyperspectral imager on the fundus camera. The image normally formed at the film camera port. During hyperspectral imaging, the image is redirected upward by a mirror. The imaging system is translated over the camera port by a linear actuator mounted below the imaging spectrograph and charge-coupled device (CCD) camera. A vertical mounting facilitated image scanning by maintaining the center of gravity of the moving components over the line of travel. A sleeve held the system at the proper height to sample the focused image. The entrance slit of the spectrograph was placed at a conjugated image plane of the eye fundus with the aid of the lens and c-mount.

Figure 2:
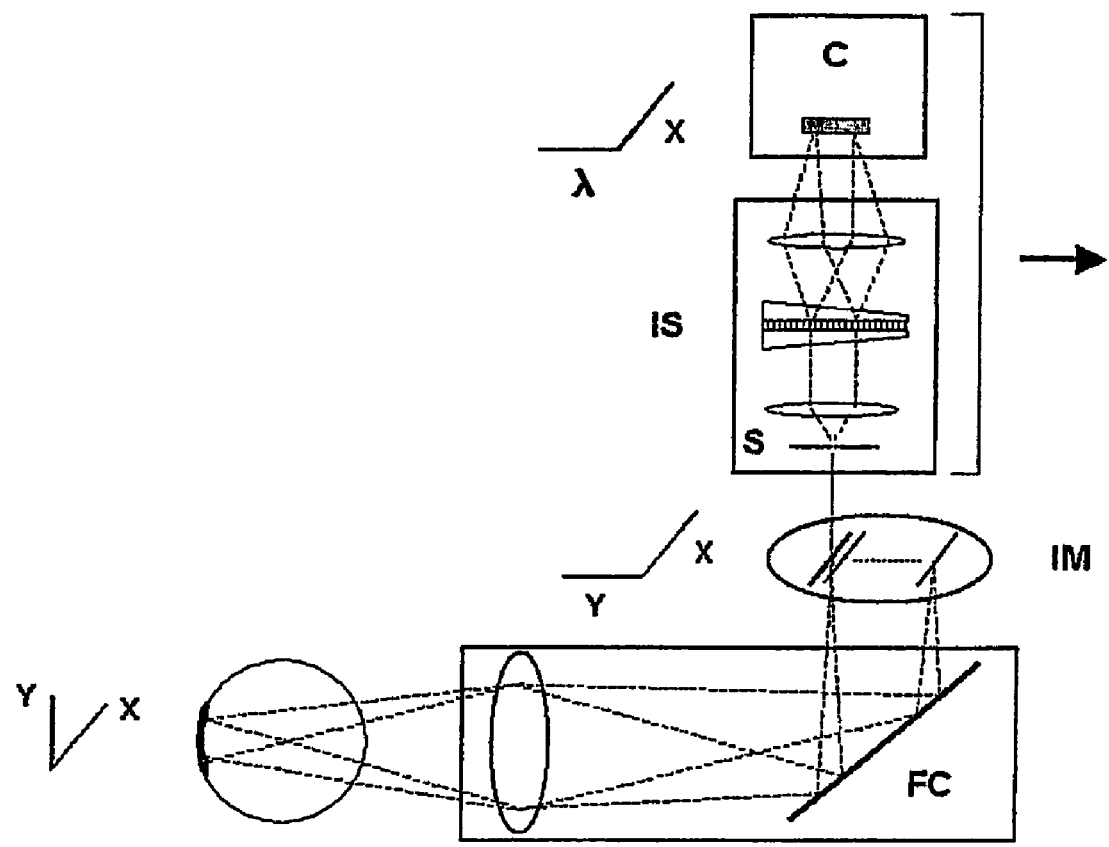
FIG. 2 illustrates an optical diagram of the retinal hyperspectral imager.

Hyperspectral Imaging. The hyperspectral images were obtained by translating an imaging spectrometer and charge-coupled device (CCD) camera (model VNIR 100, Photon Industries Inc., Stennis Space Center, Miss.) across the fundus image, as shown in FIG. 2 The area of interest on the retina is imaged with the fundus camera (FC). The dotted lines in FIG. 2 show the light collection path only. An intermediate image (IM) is formed at the slit (S) of the imaging spectrograph (IS). The spectrograph is drawn above the image for clarity. The output spectrum is focused on the sensor of the CCD camera. As the spectrograph and the camera are translated along the Y axis, the spectrum from points on consecutive lines of the image is recorded in a series of frames. Motion was controlled to create a 1:1 aspect ratio between adjacent pixels in the X direction and lines in the Y direction.

The spectrograph employed a prism-grating-prism (PGP) architecture with 2.5 nm spectral resolution (25-μm slit) and a range of 410 to 950 nm. Images of the back of the eye were acquired using the 35° viewing mode of the fundus camera. The image from the vertical camera port was focused onto the entrance slit of the spectrograph. The output spectrum was in turn focused onto the CCD image sensor. This arrangement caused the spectrum of all points along a line in the fundus image to be recorded in a single CCD frame. Frames contained a maximum of 1024 points per line and 1024 points per spectrum.

If the highest spatial or spectral resolution was not needed, greater light sensitivity could be obtained by binning CCD pixels. In the examples described below, two spatial and four spectral pixels were binned together to give spectral images containing 512 spatial points and 256 spectral bands. This resulted in sufficient light sensitivity of individual picture elements and sufficient spatial resolution to enable us to monitor oxygen-dependent spectral changes in vessels. The second spatial dimension was obtained by translating the imaging system at constant velocity in the direction transverse to the orientation of the slit. The translation system comprised two mounts attached respectively to the fundus camera and the spectrograph, and a servo-controlled actuator that provided linear motion between these parts; relative motion of this system caused the slit to remain in focus with the fundus image throughout the scan. This component is termed the focal plane scanner (FPS). The number of rows obtained in each hyperspectral image was equal to the number of frames acquired as the system was translated. The velocity of motion and the interval between frames was carefully adjusted so that adjacent pixels and adjacent rows of the image had the same spatial interval. Typically 100 rows were obtained for this study.

Figure 3:
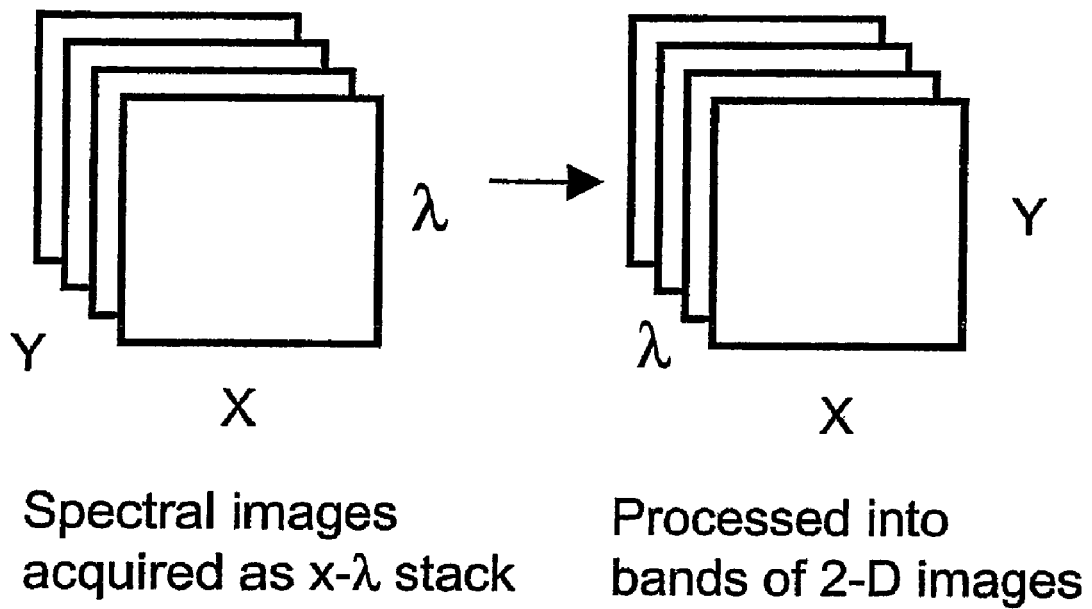
FIG. 3 illustrates the organization of spatial (x,y) and spectral (λ) information in acquired image frames (left) and after conversion to band-sequential images (right).

FIG. 3 shows the data structure of the recorded spectral images. Each frame holds the spatial (X) and spectral (λ) axis for each line of the acquired hyperspectral image (left image), with successive lines forming the Z-axis in the stack of frames. A "band-sequential" hyperspectral image is obtained by rotation of the stack of images, interchanging the Z and λ axes. After rotation, each frame contains a two-dimensional spatial image (right image) at a distinct wavelength in which intact structures are recognizable.

Extraction of Spectral Curves. Band-sequential image sets were saved from the image acquisition software (HyperVisual™; ITD, Stennis Space Center, Miss.) in ENVI image processor format (ENVI, Research Systems, Boulder, Colo.). Images were corrected for dark values by subtracting an image obtained after blocking illumination. Spectral curves were obtained in ENVI by scanning the intensity profile along the Z-axis of selected image pixels within the optical nerve head (ONH) border, corresponding to artery, vein, and surrounding ONH. For spectral curves, a five-point moving average filter was applied to individual curves of each time point, and the smoothed data were then averaged to obtain final curves that represent the spectral signatures obtained before application of high oxygen, after application of high oxygen, and before high IOP. Time points during high IOP were not averaged.

EXAMPLE 3

Mapping Relative Oxygen Saturation

Figure 4:
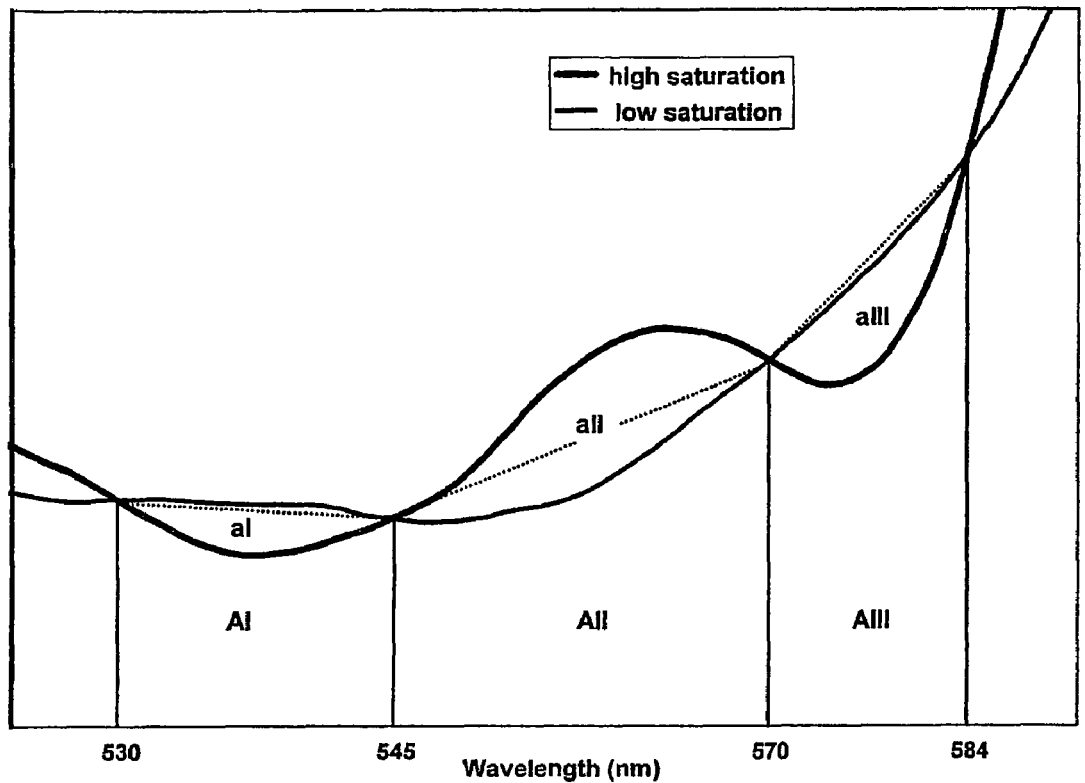
FIG. 4 illustrates the reflectance spectra of saturated blood ($HbO_2$ signature, bold curve) and desaturated blood (Hb signature, thin curve) from retinal recordings.

Reference Spectra for High and Low Oxygenation States: Relative saturation was assessed from amplitudes of the hemoglobin spectral signatures that were contained in the reflectance spectra from retinal blood. As saturation was decreased from a high to a low value, spectral minima at 542 and 577 nm from oxygenated hemoglobin ($HbO_2$ spectral signature) were converted to a single minimum at 555 nm from deoxyhemoglobin (Hb spectral signature). No changes occurred at wavelengths where $HbO_2$ and Hb spectral curves crossed (isosbestic points). These spectral features from reflectance recordings at high and low saturation are shown in FIG. 4. Although the sloping baseline produces a slight blue-shift of spectral minima, only the areas under curves are used in this method. In FIG. 4, reflectance spectra of oxygen-saturated blood ($HbO_2$ signature, bold curve) and oxygen-desaturated blood (Hb signature, thin curve) are shown from retinal recordings. The $HbO_2$ curve contains two minima corresponding to wavelengths of peak light absorption. The Hb curve contains a single broad minimum. The sloping baseline causes minima wavelengths to be shifted slightly to shorter wavelengths. Vertical lines extend from the axis to wavelengths where $HbO_2$ and Hb have equal reflectance and absorbance (isosbestic points of hemoglobin in distilled water). Dotted lines connect pairs of isosbestic points. Regions I, II, and III are defined between isosbestic points: Region I between 530 and 545 nm; Region II between 545 and 570 nm; and Region III between 570 and 584 nm. In each region, the area between the spectral curve and the dotted line is denoted as aI, aII, and aIII, respectively. AI, AII and AIII represent the areas under the dotted lines to the baseline in regions I, II, and III, respectively. Saturation maps were determined from region II (partial signature) and from the combination of regions I, II, and III (full signature).

Isosbestic points at 530, 545, 570, and 584 nm were selected from recorded spectra. As seen in FIG. 4, the curve of saturated blood passes above the line that connects the points at 545 and 570 nm (region II). The curve moves toward the line and passes below the line as the blood becomes more desaturated. This area between the spectral curve and line connecting points at 545 and 570 nm (designated "aII" in FIG. 4) is largest for 100% saturation and decreases, eventually changing sign, as the blood becomes desaturated. Changes in the total reflectance from different recordings were compensated for by dividing this saturation-sensitive area by the area between the line connecting points at 545 and 570 nm and the baseline (AII in FIG. 4). This area is proportional to the intensity of reflected light in the recorded spectrum and is not affected by saturation changes. A partial signature map of relative oxygen saturation was found from the ratio of these saturation-dependent and saturation-independent areas in region II (aII/AII). A partial signature index could be calculated using this ratio. The term partial signature refers to the use of only the region (Region II) of the spectrum between the second pair of isosbestic points.

A second method, producing a full signature saturation map, used three regions of the spectral curve as shown in FIG. 4. The first region (Region I) is defined as the region between 530 and 545 nm; the second region (Region II) is defined (as above) as the region between 545 and 570 nm; and the third region (Region III) is defined as the region between 570 and 584 nm (FIG. 4). Spectral maps were produced that included all three regions to determine if a significant reduction in noise and increase in sensitivity could be obtained by all three regions. Areas between the curve and the line connecting the isosbestic points in regions I and III were negative at high saturation and moved toward zero and even slightly positive for low saturation. This second map, referred to as a full signature map, was found by subtracting areas I and III from area II (after each area was compensated for total reflectance differences as described above for region II). The full signature map then was the ratio aII/AII minus the two ratios aI/AI and aIII/AIII. The use of the full signature gave a larger range of values for the same change in saturation and tended to average noise to a greater extent. For each type of map, values representing low to high saturation were color-coded as blue, green, yellow, and red. Because spectral changes were referenced to isosbestic points, this method minimized errors contributed by variation in the slope of the spectral baseline from different recording sites.

Relative Saturation Indices. An index of the relative oxygen saturation (RSI) was determined from separate regions of the hyperspectral image containing artery, vein, and selected areas of the ONH (see FIG. 5). For each region an average spectral curve was determined, and then the RSI was calculated by the same method described above for individual spectral curves.

EXAMPLE 4

Figure 5:
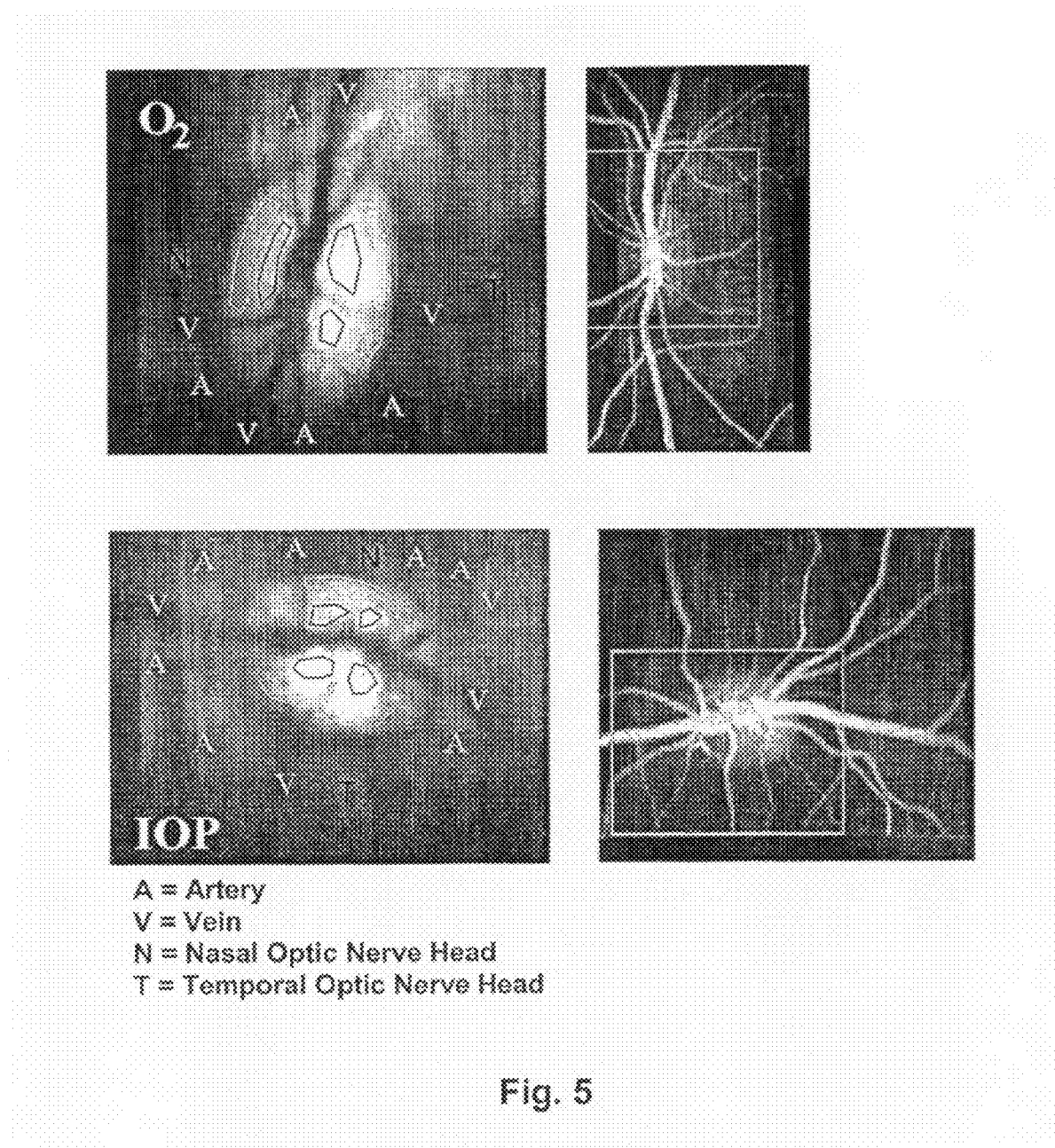
FIG. 5 illustrates, on the left side, single-band images (570 nm) of the optic nerve head (ONH) and vessels from hyperspectral images obtained for oxygen breathing (top) and intraocular pressure (bottom) experiments, with labels corresponding to the vessel type (A, artery; and V, vein), and to nasal (N) and temporal (I) aspects of the optic nerve head; and with lines indicating the optic nerve head areas, white lines for rim areas and black lines for cup areas. The right side shows flourescein angiograms (venous phase) used to confirm the vessel type (A, artery, and V, vein) for each experiment.

Results of Either Pure Oxygen or Increased Intraocular Pressure on Spectral Curves FIG. 5 shows the area of the optical nerve head (ONH) obtained from the 570 nm band in the hyperspectral image for the oxygen concentration images (top left) and the variable IOP images (bottom left). Confirmation of the vessel type was done by fluorescein angiography (images at right from the venous phase) for each experiment. Relative saturation indices in FIGS. 9 and 11 were determined from retinal vessels marked as A (artery) and V (vein), and from the ONH inside areas bounded with white lines (rim) and black lines (cup) as labeled in FIG. 5. Nasal and temporal aspects of the ONH are labeled N and T respectively.

Figure 6:
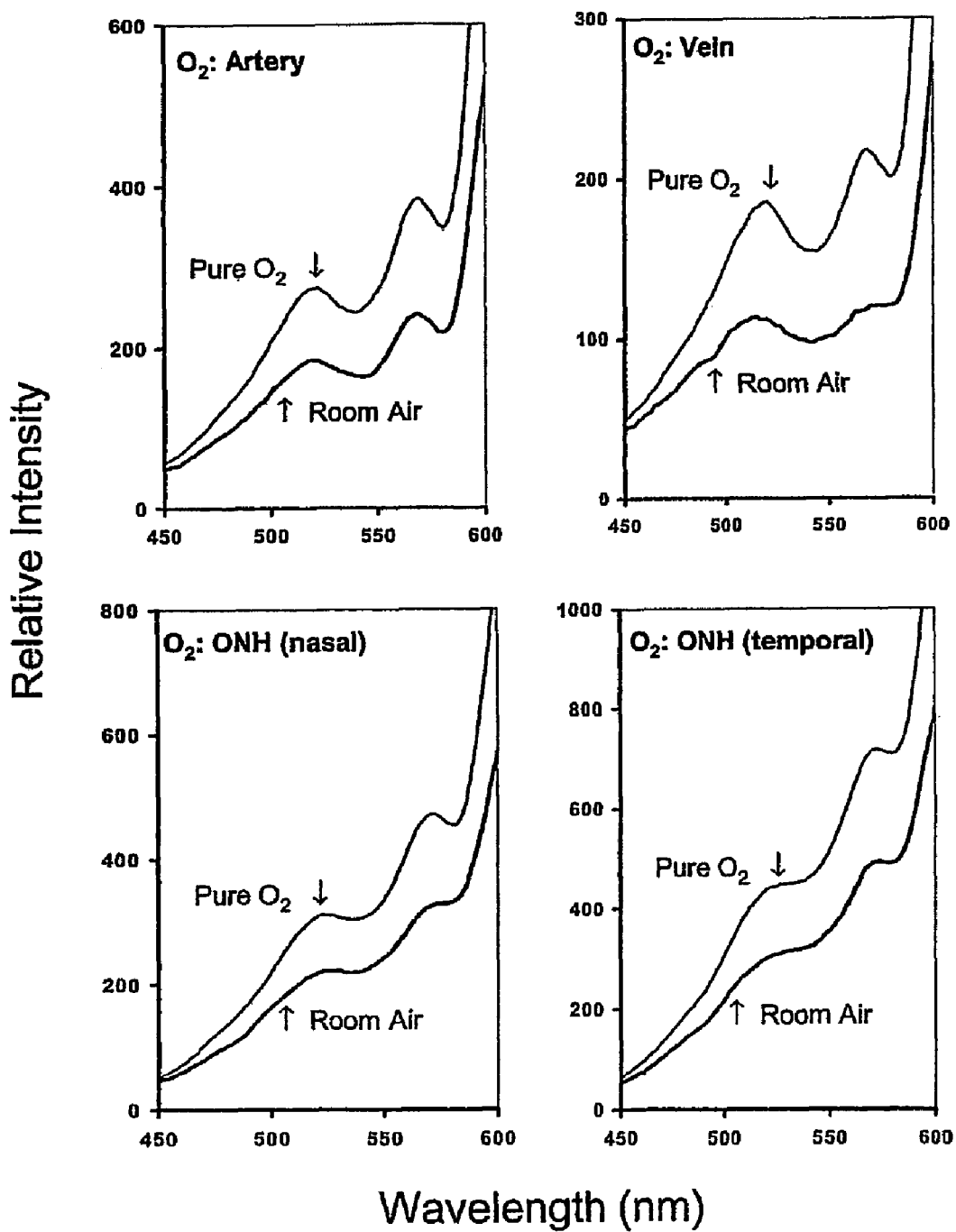
FIG. 6 illustrates the spectral curves from various locations in the eye while breathing room air and pure oxygen.
Figure 7:
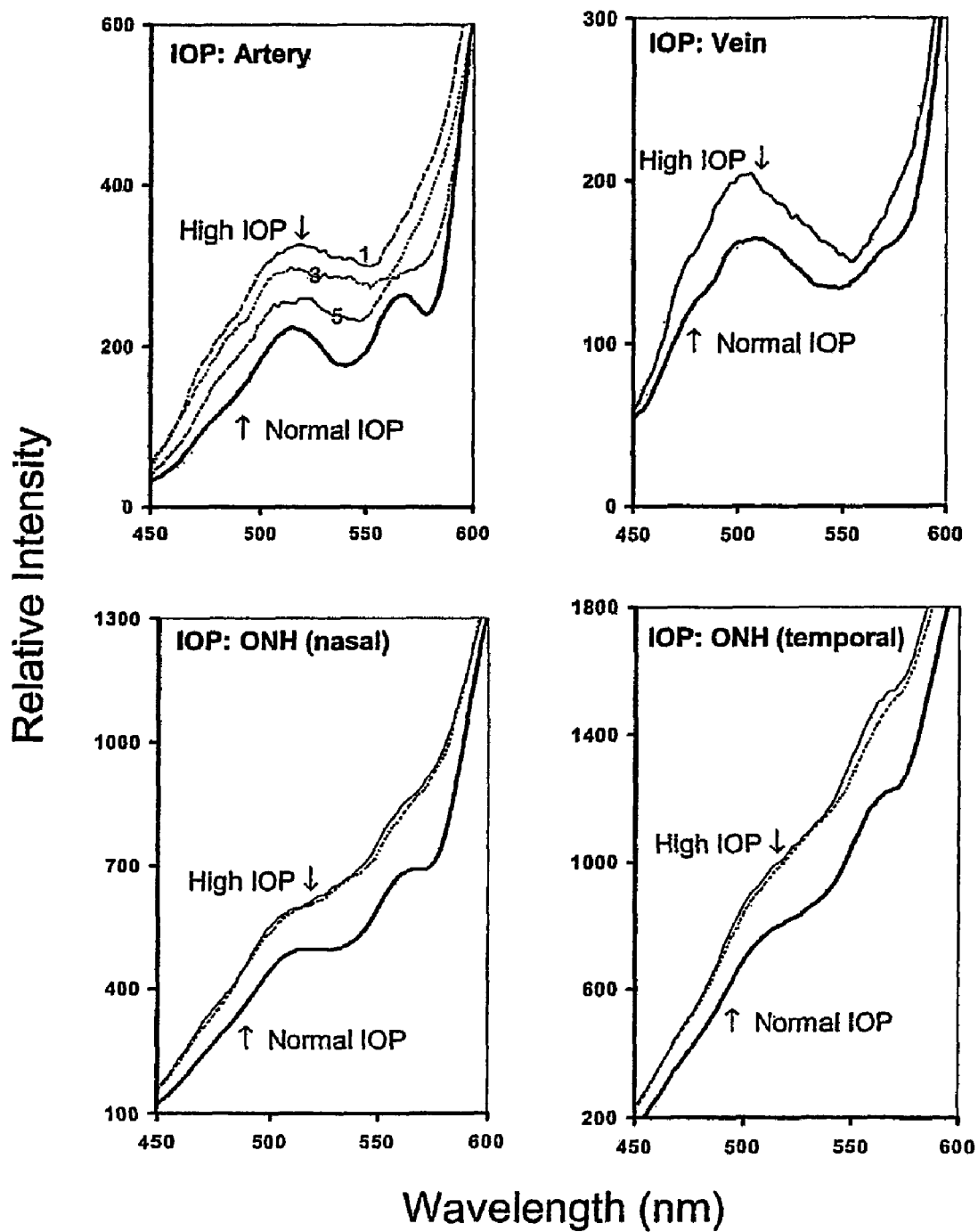
FIG. 7 illustrates the spectral curves from various locations in the eye at room pressure and at higher intraocular pressure.

Spectral Signatures. FIGS. 6 and 7 show a portion of the reflectance spectra between 450-600 nm containing the hemoglobin signature (spectral curves) from retinal artery, vein, and nasal and temporal ONH under various experimental conditions. Increased oxygen saturation is indicated in these plots when the experimental spectrum changes to more closely match the $HbO_2$ signature of FIG. 4, with stronger minima at 542 nm and 577 nm. Desaturation is indicated when the curve more closely resembles the deoxyHb signature having a single spectral minimum. Higher reflectances at the longer wavelengths result mainly from weaker light absorption at these wavelengths by choroidal pigments in the fundus. The spectral curves of both FIGS. 6 and 7 showed the expected $HbO_2$ signature in arteries and the mixed $Hb$-$HbO_2$ signature in veins under room air conditions. Switching to pure $O_2$ strengthened the $HbO_2$ signature of both types of vessels, as seen in FIG. 6. If retinal arterial saturation is closely matched to the systemic saturation (95-97%), observed increases in the $HbO_2$ signature in the artery represent only a 3-5% increase in saturation. Oxygen leakage from the ophthalmic artery could cause the retinal artery saturation to be lower than systemic levels. In that case, the response seen in the artery may represent up to an 8% increase in saturation. Since a fixed leakage rate would result in more or less arterial saturation depending on the flow rate, evaluation of retinal arterial saturation could effectively probe changes in blood flow at the major vessels supplying blood to the inner retina. The proportionately stronger $HbO_2$ signature observed in veins corresponds to significantly larger increases in venous saturation. This effect was noted previously and was attributed to inhibition of the desaturation of capillary blood in the presence of high plasma $pO_2$. See J. Hickam et al. (1966); and J. M. Beach et al. (1999).

Oxygen breathing. The effect of inspired $O_2$ concentration is shown in FIG. 6. The artery (top left) showed a small increase in the $HbO_2$ signature with pure $O_2$, relative to room air. In the vein (top right), this increase was markedly larger. Inspiration of pure $O_2$ raised total reflectance, as shown by the greater spectral amplitude. In the nasal and temporal ONH (bottom left and right), pure $O_2$ increased the $HbO_2$ signatures, but not to the degree observed in the vessels. The larger increase was in the nasal ONH spectrum. Pure $O_2$ also increased total reflectance from the ONH. All spectra from the ONH showed an increased baseline slope because of higher reflectance at red wavelengths. As expected, the overall results show increased oxygen saturation in both the large vessels and the ONH microcirculation with increased concentration of inspired $O_2$.

Intraocular pressure (IOP). The effect of increased IOP on oxygen saturation as seen in the spectral curves is shown in FIG. 7. In the artery (top left), high IOP sustained for 5 minutes gradually converted the $HbO_2$ signature to an Hb signature. Top left in FIG. 7 shows artery at normal IOP and at 1, 3, and 5 minutes after IOP was increased to 60 mm Hg. Top right shows a vein at normal IOP and 1 minute after pressure was increased to 60 mm Hg. Bottom left indicates the nasal ONH. Bottom right indicates the temporal ONH. For the high IOP curves, the dotted line represents 1 minute and the solid line represented 5 minutes after IOP was increased to 60 mm Hg. The data indicate that a deep level of desaturation occurred in the artery. In the vein (top right), the normal IOP curve shows a weak $HbO_2$ signature. Within 1 minute after the onset of high IOP, however, the curve was converted to a strong Hb signature. These results suggest that high IOP causes desaturation of the retinal blood supply in both arteries and veins. Increased IOP resulted in only modest increases in total reflectance.

In the ONH (FIG. 7, bottom left and right), $HbO_2$ spectral signatures were present at low IOP. One minute after IOP was increased to 60 mm Hg, the amplitude of the signature decreased. At 5 minutes, the nasal ONH curve was nearly parallel to that at 1 minute, whereas the temporal ONH curve showed some small restoration of the $HbO_2$ signature. These results show that high IOP reduced saturation in the ONH microcirculation but to lesser degree than in the retinal circulation, and suggest that saturation was partially restored in some regions.

EXAMPLE 5

Effect of Oxygen Breathing and IOP on Relative Oxygen Saturation

Figure 8A:
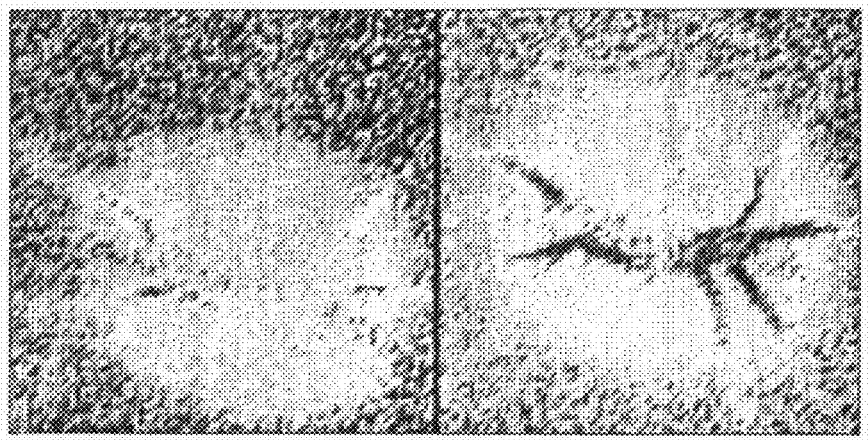
FIG. 8A illustrates partial signature saturation maps of the oxygen breathing experiment before (left, room air) and during pure oxygen breathing (right). The low to high oxygen saturation is indicated by the progression inside the blood vessel from blue (pale grey) to green to yellow (bright white) to red (almost black).
Figure 8B:
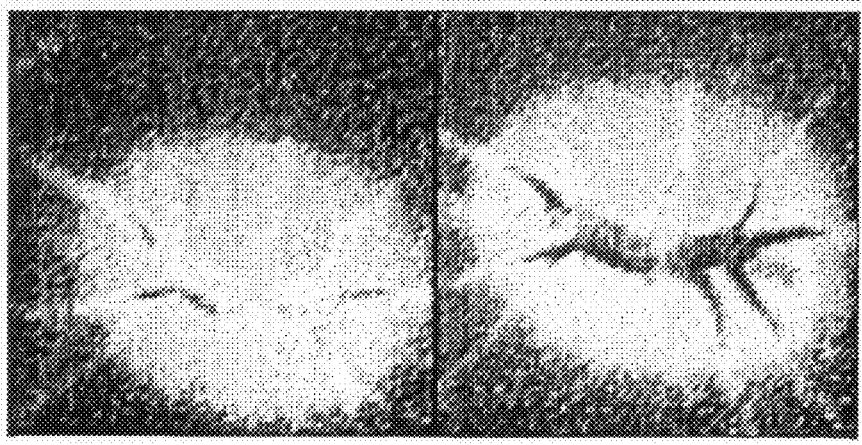
FIG. 8B illustrates full signature maps of the oxygen breathing experiment before (left, room air) and during pure oxygen breathing (right). The low to high oxygen saturation is indicated by the progression inside the blood vessel from blue (pale grey) to green to yellow (bright white) to red (almost black).

Responses to Oxygen Breathing. FIGS. 8A and 8B show spatial changes in the relative saturation of ONH structures during room air breathing (left) and 2 minutes after switching to pure oxygen (right). FIG. 8A shows maps using the partial signature method, while FIG. 8B shows maps using the full signature method. The partial signature maps (FIG. 8A) reveal saturation differences; however, structures such as the large vein are more clearly delineated during high saturation in the full signature maps (FIG. 8B, right panel). In both figures, increasing haemoglobin oxygen saturation is indicated by the progression inside the blood vessel blue (pale grey) to green to yellow (bright white) to red (almost black). Temporal to nasal orientation in each map is top to bottom. These results show that better definition of the changes was revealed in the full signature maps. Accordingly, the full signature method was used to map IOP saturation changes below, and to determine the RSIs from vessel and ONH areas.

Figure 9:
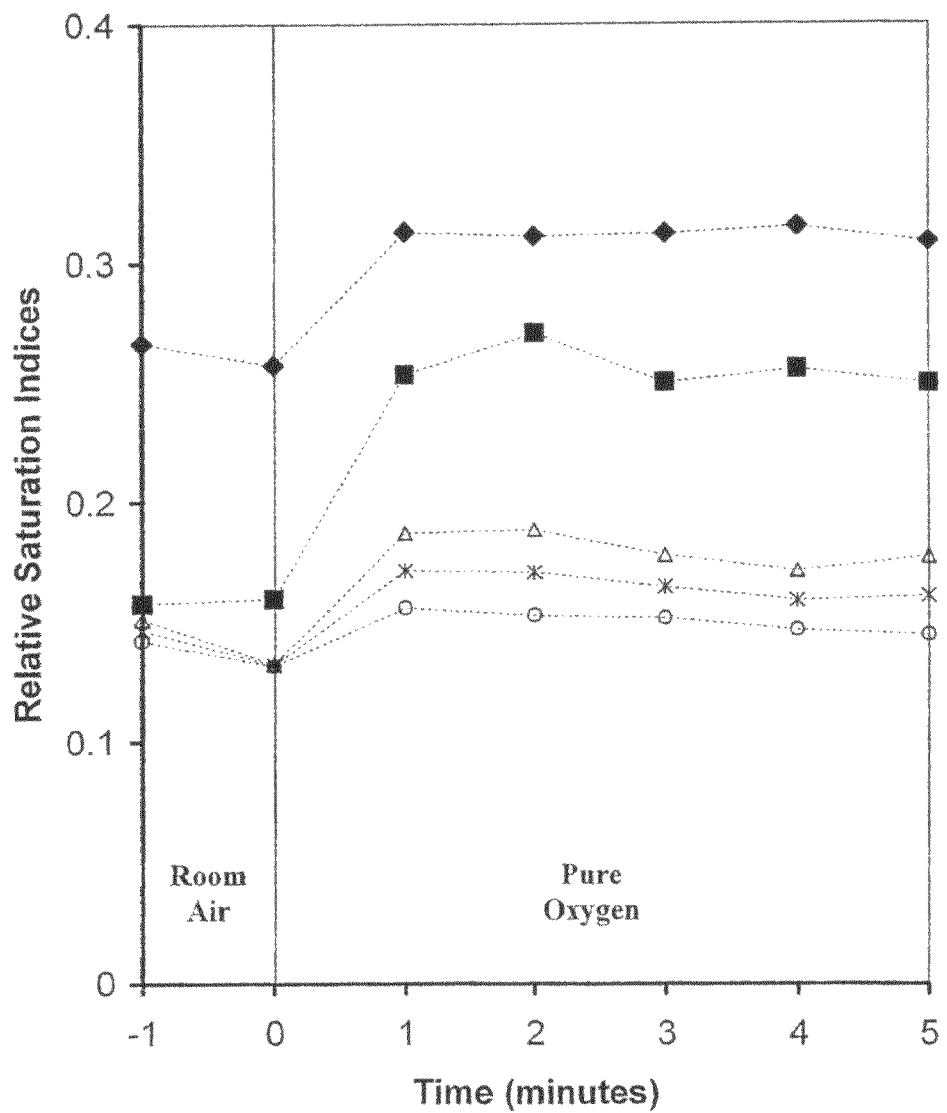
FIG. 9 illustrates the relative saturation indices (RSIs) from the oxygen breathing experiment (pure oxygen breathing started after the second data point, time=0) from retinal vessels (large symbols: artery (filled diamonds) and vein (filled rectangles)) and from optic nerve head (ONH) regions (small symbols: temporal cup (open circles), nasal cup (open triangles), and average over ONH (x)).

Under room air conditions, high saturation areas included outlines of arteries out to the ONH boundary. These vessels continued outside the ONH with a different saturation code. During pure oxygen breathing, saturation increased in the arteries, and new areas of high saturation appeared where veins were located. The ONH tissue surrounding the vessels, particularly on the nasal side, showed smaller increases in saturation. These results agree with the spectral changes shown in FIG. 6. Table 1 displays RSIs averaged over two time points for room air breathing, or over five time points for pure oxygen breathing. All structures showed significant increases ($P<0.05$) in the RSI during pure oxygen breathing (Table 1); the increase in the veins was nearly twice (factor of 1.9) that found in the artery, whereas smaller increases in the ONH (averaged over the cup and rim) were approximately half (factor of 0.52) that of the artery. A slow decrease in the saturation over time occurred RSIs calculated from the vein and ONH, but not from the artery (FIG. 9). FIG. 9 indicates the relative saturation indices (RSIs) from retinal vessels and ONH for the oxygen breathing experiment. RSIs were determined from vessel segments inside the ONH and from rim and cup regions as denoted in FIG. 5. The following symbols are used in FIG. 9: vessel segments (large symbols): artery (filled diamonds), and vein (filled rectangles); and ONH regions (small symbols): temporal (open circles), nasal (open triangles), and average over ONH (x). Breathing pure oxygen began immediately after the second data point (time=0).

TABLE 1

Relative Saturation Indices from Oxygen Experiment

| Condition | Artery | Vein | Optic Nerve Head | | |
| --- | --- | --- | --- | --- | --- |
| | | | Temporal | Nasal | Average |
| Room Air* | 0.261 ± 0.007 | 0.159 ± 0.001 | 0.137 ± 0.007 | 0.142 ± 0.013 | 0.139 ± 0.010 |
| Pure Oxygen[†] | 0.312 ± 0.002 | 0.256 ± 0.009 | 0.151 ± 0.004 | 0.180 ± 0.007 | 0.166 ± 0.006 |
| Difference[‡] | 0.051 ± 0.009 | 0.097 ± 0.010 | 0.014 ± 0.011 | 0.038 ± 0.020 | 0.027 ± 0.016 |

Unpaired samples of equal variance.
*Average over two time points during room air breathing.
[†]Average over five time points at high $O_2$.
[‡]All differences are significant (P < 0.05).
Values are means ± standard deviations.

Figure 10A:
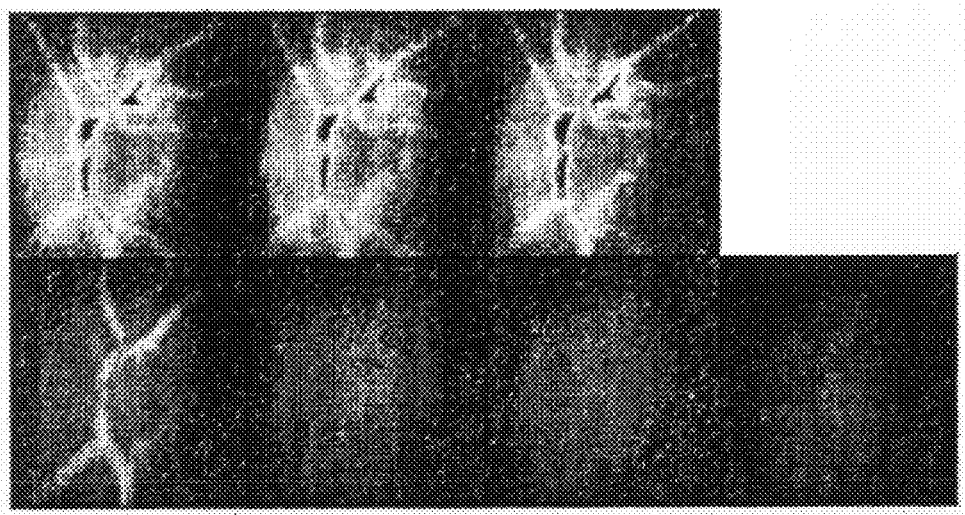
FIG. 10A illustrates full signature saturation maps of the intraocular pressure experiment with the top three maps under normal IOP conditions (15 mm Hg), and the bottom four maps under increased IOP (60 mm Hg), representing (left to right) 1, 2, 3, and 4 minutes after onset of increased pressure. The low to high oxygen saturation is indicated by the progression inside the blood vessel from blue (pale grey) to green to yellow (bright white) to red (almost black).
Figure 10B:
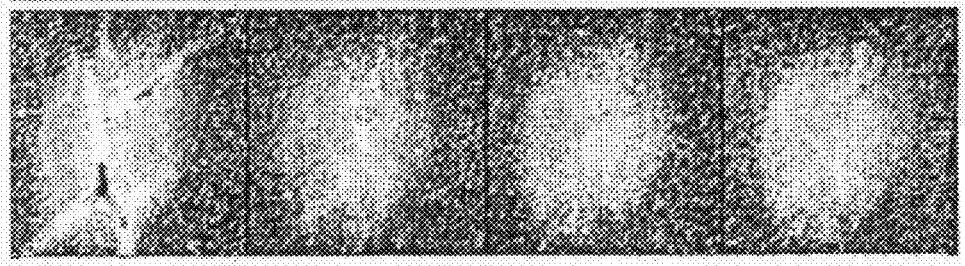
FIG. 10B illustrates full signature saturation maps of the intraocular pressure experiment with a compressed scale showing (left to right) 1, 2, 3, and 4 minutes after onset of increased IOP. The low to high oxygen saturation is indicated by the progression inside the blood vessel from blue (pale grey) to green to yellow (bright white) to red (almost black).

Responses to High IOP. Hyperspectral imaging showed good repeatability, as is evident in the full signature saturation maps in FIGS. 10A and 10B. FIG. 10A, top row, was from repeated recordings during low IOP (room pressure, 15 mm Hg). High saturation appears at artery locations within the border of the ONH and in the ONH tissue surrounding the vessels. Changes in saturation at 1 minute intervals after switching to high IOP are shown in FIG. 10A, bottom row. The bottom row (left to right) represents 1, 2, 3, and 4 minutes after the onset of high IOP (60 mm Hg). FIG. 10B represents maps using a more sensitive scale (a scale that spans a smaller range) showing (left to right) at 1, 2, 3, and 4 minutes after the onset of high IOP. Low to high saturation is indicated by the progression inside the blood vessel from blue (pale grey) to green to yellow (bright white) to red (almost black). For each map, temporal to nasal orientation is right to left.

The high saturation of the arteries and most of the ONH disappeared after 1 minute. A gradual return of saturation over the temporal ONH cup was observed from 2 through 4 minutes after IOP elevation.

Figure 11:
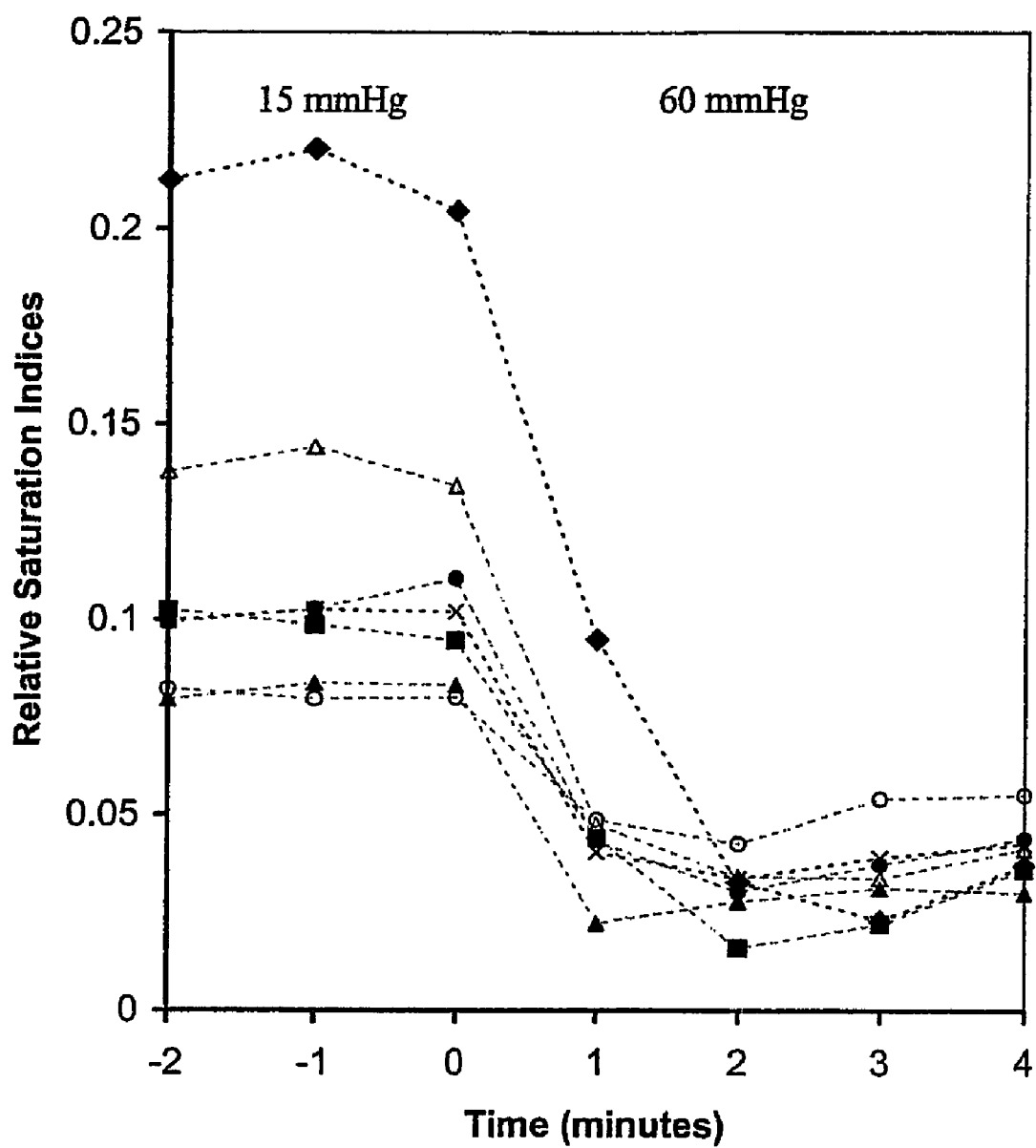
FIG. 11 illustrates the relative saturation indices (RSIs) from the intraocular pressure experiment (60 mm Hg pressure started after the third data point, time=0) from retinal vessels (large symbols: artery (filled diamonds) and vein (filled rectangles)); and from optic nerve head (ONH) regions (small symbols: temporal cup (open circles), nasal cup (open triangles), and average over ONH (x)).

Relative saturation indices are given in FIG. 11 and Table 2 for the IOP experiment. Table 2 displays RSIs averaged over three time periods for normal IOP, and over two time points for high IOP. High IOP resulted in significant reduction ($P<0.05$) of the RSI; for each structure. After 3 minutes of high IOP, the values from artery and vein were not significantly different from one another. In the temporal ONH cup, the RSI decreased initially, but then recovered 24% of its original normal IOP value within the 4-minute high IOP period. This phenomenon was not observed in other areas of the ONH. FIG. 11 indicates relative saturation indices from retinal vessels and ONH for IOP experiment. The following symbols are used in FIG. 11: vessel segments (large symbols): artery (filled diamonds), and vein (filled rectangles); and ONH regions (small symbols): nasal cup (open triangles), temporal cup (open circles), nasal rim (filled triangles), temporal rim (filled circles), and average over ONH (x). High IOP begins immediately after third point (time=0).

TABLE 2

Relative Saturation Indices from IOP Experiment

| Condition | Artery | Vein | Averaged ONH | Temporal cup |
|---|---|---|---|---|
| Normal IOP* | 0.210 ± 0.008 | 0.139 ± 0.005 | 0.101 ± 0.001 | 0.081 ± 0.001 |
| High IOP† | 0.030 ± 0.01 | 0.029 ± 0.01 | 0.041 ± 0.002 | 0.054 ± 0.001 |
| Difference | 0.180 ± 0.018 | 0.110 ± 0.015 | 0.060 ± 0.003 | 0.027 ± 0.002 |

Unpaired samples of equal variance.
*Average over three time points at normal IOP.
†Average over last two time points at high IOP.
‡All differences are significant ($P < 0.05$).
Values are means ± standard deviations.

$HbO_2$ signatures were also obtained from areas between vessels within the border of the ONH. Since the light probe is in the green-red spectral range, these readings were interpreted to be signatures of blood carried by the microcirculation near the surface nerve fiber layer. It is also possible that some of this signal resulted from light first passing through surface vessels and then returning through the microcirculation of the surrounding tissue. Pure $O_2$ strengthened the $HbO_2$ signature in the ONH, but to a lesser degree than that observed in the vein, as expected if this signature represents the averaged blood saturation in the microcirculation. These results are the first report of measurements of oxygen saturation changes in the ONH microcirculation using non-invasive reflectance imaging.

Under pure $O_2$ conditions, the ONH and vessel reflectance at the hemoglobin absorption wavelengths was consistently greater than under room air conditions. This effect may be the result of vasoconstriction under high $O_2$ that reduces the luminal blood volume in the surface vessels and, correspondingly, the perfusion of the microcirculation. The features of the spectral profiles of vessels and tissue are thus in agreement with changes anticipated when the vascular supply of $O_2$ is increased.

Since metabolic changes associated with progression of retinal disorders presumably alter the oxygen utilization in the tissues, venous saturation maps should be a sensitive probe for disease states. Saturation maps determined by assessment of the Hb and $HbO_2$ spectral signatures, in particular the relative contributions of the Hb and $HbO_2$ spectral peaks between isosbestic points, were able to monitor the venous saturation increases in response to breathing pure $O_2$. Previous work estimated these increases in the range 8-23%. If changes of similar size are present during the state of hypoxia, maps drawn as indicated above should be able to isolate hypoxic areas when the scale is moved to operate over the lower venous saturation range. Calibration for different saturation ranges would make the maps more sensitive in low and high saturation regions.

Raising IOP to 60 mm Hg had essentially the opposite effect on blood saturation. At this IOP, the perfusion pressure is very low. Arterial desaturation could have resulted from a slowing or stoppage of flow caused by collapse of the vessel under pressure, during which time oxygen diffused from the vessel. The more rapid appearance of the Hb signature in the veins was likely due to lower initial saturation of venous blood. An interesting feature of the high IOP response was partial recovery of saturation in the ONH microcirculation while the pressure remained high. Saturation recovery was seen near the cup of the ONH, which was temporal with respect to the origin of the vessels. The full signature map reduced noise enough to allow good visualization of this recovery. Since the high IOP effectively occluded the surface vessels, the source of oxygen is most probably from deeper levels of the circulation, which includes the retrolaminar layer. Increased reflectance during high IOP can be explained by low blood volume, since high IOP would partially occlude the major surface vessels and vessels feeding the outer ONH microcirculation, causing this area to blanch.

Hyperspectral Imaging. These results demonstrate the ability of hyperspectral imaging to measure relative changes in oxygen saturation of blood vessels, e.g., retinal macro- and microcirculation. The usefulness of relative measurements of the oxygen saturation for assessing the vascular response to controlled changes in oxygen supply and utilization is evident from these data.

The present hyperspectral imaging technique enables spectral quantitation to be carried out over two dimensions on the ONH, allowing regional changes in saturation to be identified. Different saturation color codes from retina outside the ONH were obtained. This difference may reflect disparate amounts of light being scattered into vessels from the pigment-free ONH and pigmented retina. In addition to the current method of curve integration, other spectral quantitation methods, such as curve fitting, can be employed. Significantly faster recording techniques would be better to achieve a more clinically acceptable method for mapping spectral information on the ocular fundus.

Hyperspectral imaging used with the current method can provide a much needed diagnostic tool for prevention and treatment of retinal disorders. The desired goal is the successful application of therapeutic interventions before irreversible damage occurs. One potential gain for detecting abnormalities in the oxygen saturation response is significantly earlier diagnosis of glaucoma. It is presently believed that autoregulation of blood flow is impaired in glaucomatous disease, possibly as a result of anatomical vascular impairment of the retina and the ONH. With this technique, problems in auto-regulation could be diagnosed at an early stage, during the pre-onset stages of early phase glaucoma. In addition changes in oxygen saturation caused by other problems, e.g., diabetic retinopathy, hypertension, sickle cell anemia, and vascular diseases, can be detected by this method. In addition, this technique can be used to monitor oxygen saturation changes or blood flow in blood vessels from other body tissues, e.g., the skin, tongue, or intestine. The technique can also be used to assess skin disorders that might affect blood flow, e.g., a wound, a burn, or rosacea. The technique can be used to identify and locate major blood vessels in various regions of the body.

The complete disclosure of all references cited in this specification are hereby incorporated by reference. Also incorporated by reference are the complete disclosures of the following: B. Khoobehi et al., "Hyperspectral Imaging of oxygen saturation in the optic nerve head, retina, and choriod," Abstract presented May 7, 2003 at Association for Research in Vision and Opthalmology; B Khoobehi et al., "Non-invasive measurement of oxygen saturation in optic nerve head tissue," Proc. SPIE, vol. 5325, pp. 104-110, Optical Diagnostics and Sensing IV; June 2004; and B. Khoobehi et al., "Hyperspectral imaging for measurement of oxygen saturation in the optic nerve head," Investigative Opthalmology and Visual Science, vol. 45, pp. 1464-72 (2004). In the event of an otherwise irreconcilable conflict, however, the present specification shall control.

What is claimed:

1. A method for determining hemoglobin oxygen saturation in a tissue in vivo; said method comprising the steps of:
   (a) measuring the visible reflectance spectrum or the visible absorbance spectrum of the tissue in vivo over at least a portion of the range of wavelengths between 530 nm and 584 nm;
   (b) determining one or more of the values x, y, and z, wherein:
      (i) x is proportional to the integral of {the reference stratum minus the measured visible spectrum} over at least a portion of region I;
      (ii) y is proportional to the integral of {the measured visible spectrum minus the reference stratum} over at least a portion of region II;
      (iii) z is proportional to the integral of {the reference stratum minus the measured visible spectrum} over at least a portion of region III;
      (iv) region I is the region of the visible spectrum between the hemoglobin isosbestic point at about 530 nm and the hemoglobin isosbestic point at about 545 nm;
      (v) region II is the region of the visible spectrum between the hemoglobin isosbestic point at about 545 nm and the hemoglobin isosbestic point at about 570 nm;
      (vi) region III is the region of the visible spectrum between the hemoglobin isosbestic point at about 570 nm and the hemoglobin isosbestic point at about 584 nm;
      (vii) the reference stratum comprises a sequence of three linear segments: a first linear segment connecting the visible reflectance or absorbance of hemoglobin at the isosbestic point at about 530 nm to the visible reflectance or absorbance of hemoglobin at the isosbestic point at about 545 nm; a second linear segment connecting the visible reflectance or absorbance of hemoglobin at the isosbestic point at about 545 nm to the visible reflectance or absorbance of hemoglobin at the isosbestic point at about 570 nm; and a third linear segment connecting the visible reflectance or absorbance of hemoglobin at the isosbestic point at about 570 nm to the visible reflectance or absorbance of hemoglobin at the isosbestic point at about 584 nm;
   whereby:
      (viii) larger values of x, y, or z correspond to higher hemoglobin oxygen saturation in the tissue in vivo, and lower values of x, y, or z correspond to lower hemoglobin oxygen saturation in the tissue in vivo.

2. The method of claim 1, wherein:
   (i) x is proportional to the integral of {the reference stratum minus the measured visible spectrum} over region I;
   (ii) y is proportional to the integral of {the measured visible spectrum minus the reference stratum} over region II; and
   (iii) z is proportional to the integral of {the reference stratum minus the measured visible spectrum} over region III.

3. The method of claim 2, additionally comprising the step of determining the sum $S=x+y+z$; whereby larger values of S correspond to higher hemoglobin oxygen saturation in the tissue in vivo, and lower values of S correspond to lower hemoglobin oxygen saturation in the tissue in vivo.

4. The method of claim 3, wherein:
   (i) the value of x is corrected by a factor proportional to the integral of {the reference stratum minus the baseline} over region I; wherein the baseline corresponds to zero reflectance or zero absorbance;
   (ii) the value of y is corrected by a factor proportional to the integral of {the reference stratum minus the baseline} over region II; and
   (i) the value of z is corrected by a factor proportional to the integral of {the reference stratum minus the baseline} over region III.

5. The method of claim 1, wherein:
   (i) the value of x is corrected by a factor proportional to the integral of {the reference stratum minus the baseline} over the same portion of region I that is used to determine x; wherein the baseline corresponds to zero reflectance or zero absorbance;
   (ii) the value of y is corrected by a factor proportional to the integral of {the reference stratum minus the baseline} over the same portion of region II that is used to determine y; and
   (i) the value of z is corrected by a factor proportional to the integral of {the reference stratum minus the baseline} over the same portion of region III that is used to determine z.

6. The method of claim 1, wherein the tissue is a blood vessel.

7. The method of claim 1, wherein the tissue is skin.

8. The method of claim 1, wherein the tissue is a retina or a blood vessel in a retina.

9. A method comprising repeating the method of claim 1 at a plurality of locations in the tissue, and plotting the inferred hemoglobin oxygen saturation levels in the tissue as a function of location.

10. A method of producing a plot according to claim 9 wherein the plot shows inferred hemoglobin oxygen saturation levels in a tissue.

11. A method to enhance the visual delineation of blood vessels in a tissue, said method comprising conducting the method claim 9 on the tissue, wherein the plot of hemoglobin oxygen saturation levels as a function of location delineates the location of the blood vessels.

12. A method for diagnosing abnormal hemoglobin oxygen saturation in a tissue, said method comprising conducting the method of claim 1 on the tissue, and identifying any abnormal values of x, y, or z as indicating abnormal hemoglobin oxygen saturation in the tissue.

13. The method of claim 12, wherein the diagnosis is conducted in a patient or in a tissue having a condition selected from the group consisting of glaucoma, diabetic retinopathy, hypertension, sickle cell disease, vascular disease, skin disorder, a wound, and a burn.

\* \* \* \* \*